(12) United States Patent
Boese et al.

(10) Patent No.: US 8,295,434 B2
(45) Date of Patent: Oct. 23, 2012

(54) X-RAY IMAGING METHOD AND X-RAY IMAGING SYSTEM

(75) Inventors: Jan Boese, Eckental (DE); Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 221 days.

(21) Appl. No.: 12/890,775

(22) Filed: Sep. 27, 2010

(65) Prior Publication Data

US 2011/0075804 A1 Mar. 31, 2011

(30) Foreign Application Priority Data

Sep. 29, 2009 (DE) .......................... 10 2009 043 423

(51) Int. Cl.
*G01N 23/04* (2006.01)
(52) U.S. Cl. .......................................................... 378/62
(58) Field of Classification Search ................ 378/4, 19, 378/62, 98.8, 147
See application file for complete search history.

(56) References Cited

U.S. PATENT DOCUMENTS

| | | | |
|---|---|---|---|
| 4,803,714 A | 2/1989 | Vlasbloem | |
| 6,229,870 B1 | 5/2001 | Morgan | |
| 6,553,096 B1 | 4/2003 | Zhou et al. | |
| 6,733,176 B2 | 5/2004 | Schmitt | |
| 7,359,484 B2 | 4/2008 | Qiu et al. | |
| 7,826,594 B2 * | 11/2010 | Zou et al. | 378/92 |
| 7,885,375 B2 * | 2/2011 | Bernard De Man et al. | 378/9 |
| 2005/0135550 A1 | 6/2005 | Man et al. | |
| 2008/0260093 A1 | 10/2008 | Bontus | |
| 2010/0034450 A1 | 2/2010 | Mertelmeier | |
| 2010/0061512 A1 * | 3/2010 | Edic et al. | 378/71 |
| 2010/0091940 A1 * | 4/2010 | Ludwig et al. | 378/22 |
| 2010/0260317 A1 * | 10/2010 | Chang et al. | 378/62 |
| 2010/0329424 A1 * | 12/2010 | Harding et al. | 378/71 |

FOREIGN PATENT DOCUMENTS

DE 102008004473 A1 7/2009

OTHER PUBLICATIONS

Xintek, Inc. Nanotechnology Innovations, Xintek's Field Emission X-Ray Technology; pp. 1-8, (2004).
http://www.xintek.com/products/xray/index.htm, "Carbon Nano Tube Based Field Emission X-Ray Tubes", pp. 1-2, (2004).
Liu et al., "An Alternate Line Erasure and Readout (ALER) Method for Implementing Slot-Scan Imaging Technique with a Flat-Panel Detector—Initial Experiences", IEEE Trans Medical Imaging, Apr. 2006, pp. 496-502, vol. 24 (4).
Kunio Doi et al., "Digital radiographic imaging system with multiple-slit scanning x-ray beam: preliminary report", Nov. 1986 Radiology, 161, pp. 513-518; Magazine.

* cited by examiner

*Primary Examiner* — Irakli Kiknadze

(57) ABSTRACT

A method for recording an x-ray image with an x-ray imaging system having an x-ray source and an x-ray detector is provided. The x-ray source has a plurality of x-ray emitters arranged alongside one another. Each x-ray emitter is assigned to a part area of the x-ray detector. The x-ray beam generated by the x-ray emitter is collimated onto the assigned part area. A first x-ray emitter is activated for emitting a first x-ray beam onto a first part area and image data of the first part area is read out. Subsequently a further x-ray emitter for emitting a further x-ray beam onto a further part area of is activated and image data of the further part area is read out. The steps are repeated until image data for all part areas of the x-ray detector is read out. The read out image data is combined into an x-ray image.

12 Claims, 3 Drawing Sheets

X-RAY IMAGING METHOD AND X-RAY IMAGING SYSTEM

CROSS REFERENCE TO RELATED APPLICATIONS

This application claims priority of German application No. 10 2009 043 423.2 filed Sep. 29, 2009, which is incorporated by reference herein in its entirety.

FIELD OF THE INVENTION

The invention relates to a method for recording an x-ray image with an x-ray imaging system as well as to a device for carrying out such a method.

BACKGROUND OF THE INVENTION

X-ray radiography systems are used for diagnostic imaging, whereby they provide image data of a region of a patient's body to be examined in order to make possible or to simplify a medical diagnosis. The image data is obtained with the aid of an x-ray source and an x-ray-sensitive x-ray detector. A modern digital x-ray system is described in U.S. Pat. No. 6,733,176 for example.

A problem with x-ray imaging is that the image quality is adversely affected by what is known as radiation scatter. Radiation scatter occurs when x-ray radiation not only strikes the x-ray detector on a direct path from the x-ray focus through the object under examination but is also scattered in the object under examination. The scattered radiation frequently overlays the actual x-ray image and with specific images can account for up to 80% of the detected radiation. The scattered radiation is routinely reduced by what is known as an anti-scatter grid. In the simplest case this involves a plate disposed in front of the x-ray detector with x-ray-absorbing septa which are aligned to the x-ray detector and which filter out the scattered radiation. Anti-scatter grids have the problem however that on the one hand they still let through part of the scattered radiation and on the other hand they also absorb a significant part of the direct x-ray radiation (up to 50%). This additionally increases the exposure of a patient to x-rays.

Another way of reducing the scattered radiation is what is known as slot scanning. In such cases a slot-shaped x-ray beam is generated which is moved by movable collimators over the entire imaging area. On the detector side only the narrow area is screened out by a further collimator so that the scattered radiation can be very greatly reduced. An x-ray imaging system with a scanning tube is described in U.S. Pat. No. 4,803,714 for example.

Despite greatly improving radiation scatter, slot scanning systems have as yet not become established. The main reason for this is the high outlay for the mechanical movement of tube-side collimator and detector-side collimator. A new approach for flat panel detectors is described in Liu et. al: "An Alternate Line Erasure and Readout (ALER) Method for Implementing Slot-Scan Imaging Technique With a Flat-Panel Detector—Initial Experiences", IEEE Trans. Med. Imaging 2006, April 25(4), pp. 496-502. This system uses an "electronic collimation" on the detector side, with the detector lines not directly irradiated being discarded. However this system still needs a mechanically-movable tube-side collimator.

SUMMARY OF THE INVENTION

The object of the present invention is to provide a slot-scan method which makes do without mechanically-movable collimators and makes a simple and effortless recording of an x-ray image possible. Furthermore an object of the invention is to provide an x-ray device suitable for carrying out the method.

The object is inventively achieved by a method for recording an x-ray image with an x-ray imaging system and by a device in accordance with the independent claims. Advantageous embodiments of the invention are the subject matter of the associated dependent claims in each case.

The inventive method of recording an x-ray image with an x-ray imaging system with x-ray source and an x-ray detector, with the x-ray source featuring a plurality of x-ray emitters arranged next to one another, with each x-ray emitter being assigned a part area of the x-ray detector and the x-ray beam generated by the respective x-ray emitter being collimated onto the assigned part area, comprises the following steps:

a) A first x-ray emitter is activated for emitting a first x-ray beam onto a first part area of the x-ray detector assigned to it and image data of the first part area of the x-ray detector is read out.

b) Subsequently a further x-ray emitter for sending out a further x-ray beam to a further part area of the x-ray detector assigned to it is activated and image data of the further part area of the x-ray detector is read out.

c) Step b) is repeated until such time as image data is read out for all intended part areas, especially all part areas of the x-ray detector, and d) The image data of the read-out part areas is combined into an x-ray image.

The inventive method thus replaces known slot scanning methods and is able to be carried out more quickly and more easily through the sequential activation of the x-ray emitters and their already pre-collimated x-ray emitters. The recording time is greatly reduced since this is no longer dictated by the mechanical movement of the collimator but only by the tube power of the x-ray emitter and by the read-out time of the x-ray detector. In addition scattered radiation can be almost completely avoided by the inventive method and thus high-quality x-ray images can be created.

In accordance with an embodiment of the invention the respective x-ray emitters are collimated in a slot shape onto the respective assigned part areas. The respective part areas especially comprise between one and ten complete pixel lines of the x-ray detector. In particular the part areas do not intersect but adjoin each other contiguously.

In an advantageous manner, for a complete recording of the x-ray detector, all part areas together give the active overall surface of the x-ray detector, i.e. the complete usable surface for image generation.

In accordance with the further embodiment of the invention adjacent x-ray emitters are sequentially activated in turn, with two or more x-ray emitters never being activated simultaneously in order not to generate any scattered radiation. As an alternative a different activation sequence can be selected. Expediently x-ray emitters disposed adjacent to each other in each case are assigned to adjacent part areas in order to guarantee an optimum illumination of the part areas, with x-ray beams hitting said areas at an angle which is as perpendicular as possible.

In accordance with a further embodiment of the invention the areas other than the respectively irradiated part area of the x-ray detector are not read out or alternately data is read out from all areas and the read-out data which does not originate from the part area is discarded. In this way only image data from the directly irradiated part areas is received in each case and can subsequently be assembled into a complete x-ray image.

To carry out the inventive method a medical x-ray imaging system with an x-ray source and an x-ray detector is provided, with the x-ray source featuring a plurality of x-ray emitters arranged next to one another. In this case the x-ray emitters can be formed in each case by a field emission gun with a field emission cathode. Such field emission guns can be made especially small and light. In accordance with a further embodiment of the invention the field emission cathodes are formed on the basis of carbon nanotubes (so called. CNT cathodes). These types of material exhibit an especially good emission characteristic but are also stable with high currents and can also be manufactured especially small. In an advantageous manner the field emission guns are arranged as a linear array. This array is disposed so that a simple assignment to the respective, especially row-type, part areas of the x-ray detector is possible.

BRIEF DESCRIPTION OF THE DRAWINGS

The invention, as well as further advantageous embodiments in accordance with features of the dependant claims, will be explained in greater detail below on the basis of schematic diagrams of exemplary embodiments in the drawing, without the invention being restricted to these exemplary embodiments in any way. The figures show:

DETAILED DESCRIPTION OF THE INVENTION

Figure 1:
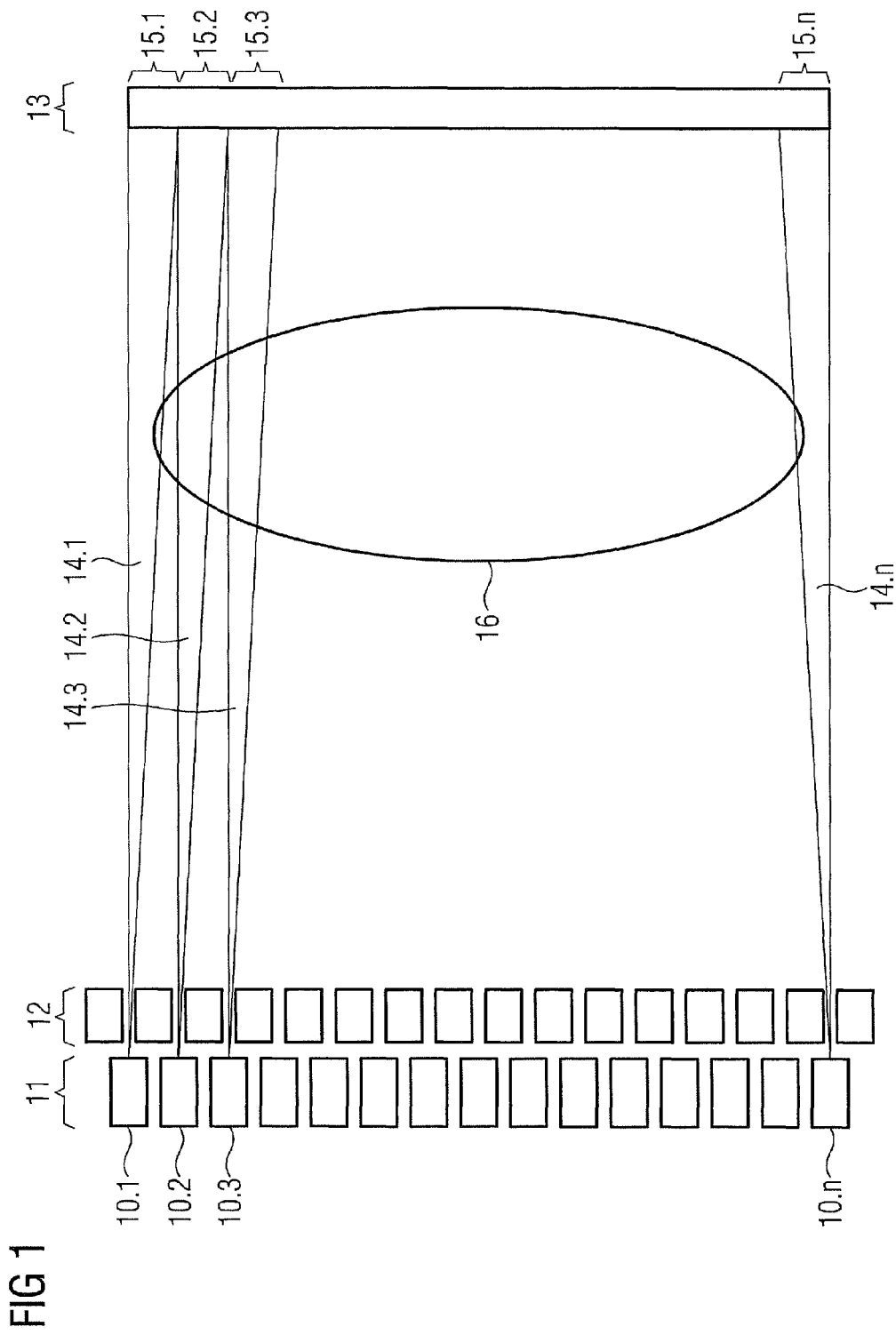
FIG. 1 a view of an x-ray imaging system with x-ray emitters and assigned part areas of an x-ray detector, FIG. 2 a sequence of steps of an inventive method, and FIG. 3 a further view of an x-ray imaging system with x-ray beam and scattered radiation.

FIG. 1 shows an inventive x-ray imaging system with an x-ray source 11 in the form of a plurality of x-ray emitters 10, especially field emission guns, and a digital x-ray detector 13, with part areas 15 of the x-ray detector assigned in each case to the x-ray emitters 10. The x-ray emitters 10 are arranged alongside one another in a linear array. Each x-ray emitter 10 is embodied to emit an x-ray beam 14, with the x-ray beams 14 being formed by a collimator 12 into slots, so that each x-ray beam 14 strikes a part area of 15 of the x-ray detector. The collimation by means of the collimator can be set when the x-ray imaging system is commissioned or the device can already have a fixed setting on delivery. The digital x-ray detector especially involves a known digital solid-state detector based on direct or indirect conversion of x-rays into an electrical charge.

A first x-ray beam 14.1 created by a first x-ray emitter 10.1 is formed in this case by the collimator 12 or by a first collimator element such that it irradiates a first part area 15.1 of the x-ray detector 13. A second x-ray beam 14.2 generated by a second x-ray emitter 10.2 arranged next to the first x-ray emitter 10.1 is formed by a collimator 12 or by a second collimator element respectively such that it can irradiate a second part area 15.2 of the x-ray detector, especially an area lying next to the first part of area 15.1. A third x-ray emitter 10.3 which in its turn is disposed next to the second x-ray emitter 10.2, generates a third x-ray beam 14.3, which can irradiate a third part area 15.3 of the x-ray detector. The x-ray source 11 has a total of n x-ray emitters and the x-ray detector also has n part areas, which together can be completely irradiated by the n x-ray emitters in order to record an image of an object under examination 16. In particular the part areas adjoin each other contiguously in this case. A part area can in such case be embodied for example such that it comprises one or more, for example two, five or ten complete lines of the x-ray detector.

Figure 2:
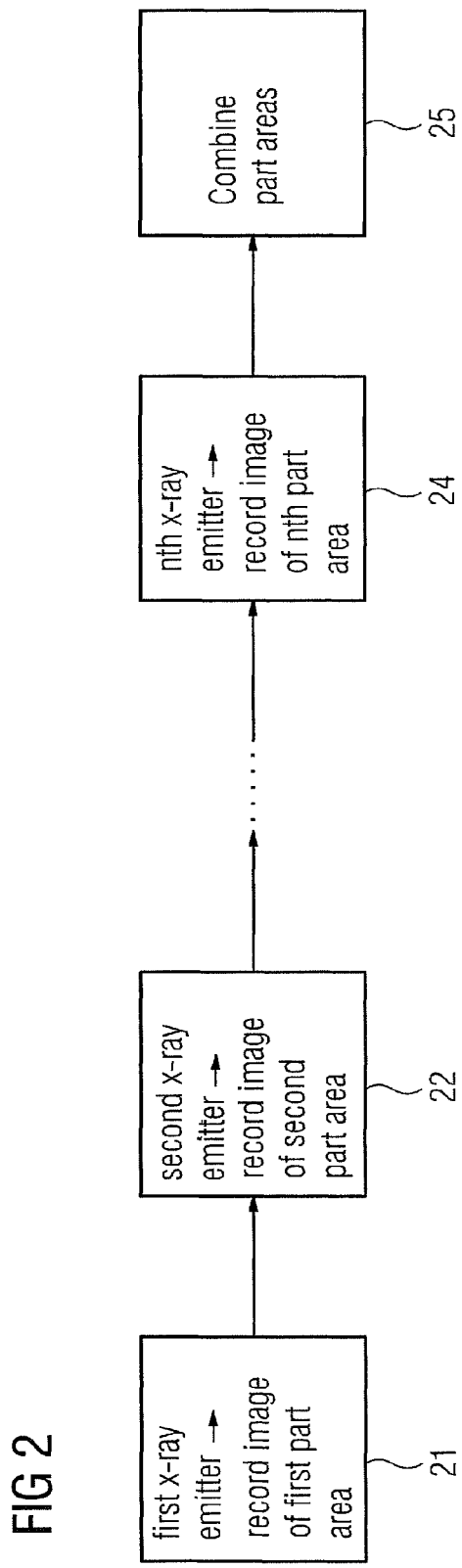

A possible sequence of the inventive method is shown for example in FIG. 2. In a first step 21 a first x-ray emitter 10.1 is activated to emit out a first x-ray beam 14.1 onto a first part area 15.1; the first x-ray beam 14.1 is collimated in this case so that it merely irradiates the first part area 15.1. The irradiated part area 15.1 of the x-ray detector is read out and all other areas of the x-ray detector are not read out. As an alternative the entire x-ray detector can also be read out and can discard the data of all areas except for the first part area 15.1. In a second step 22 a second x-ray emitter 10.2 is subsequently activated to emit a second x-ray beam 14.2 onto a second part area 15.2; the second x-ray beam 14.2 is collimated in this case so that it merely irradiates the second part area 15.2. The irradiated second part area 15.2 is then read out or alternately all areas are read out and only the data of the second part area 15.2 is not discarded. The second activated x-ray emitter is especially arranged adjacent to the first x-ray emitter; but any other given x-ray emitter can also be activated as the second emitter. The x-ray emitter adjacent to an x-ray emitter especially also has a part area assigned to it adjacent to the assigned part area; however a different assignment can also be provided.

In further steps further x-ray emitters are subsequently activated sequentially to emit x-ray beams in the same way and further part areas are irradiated and read out, up to an nth step 24, in which an nth x-ray emitter 14.$n$ is activated and an nth part area 15.$n$ of the x-ray detector is irradiated and read out. After all part areas provided for recording the area under examination are read out, in a last step 25 the image data of all part areas is combined. This can be carried out for example by means of an image system which is assigned to the x-ray imaging system.

Figure 3:
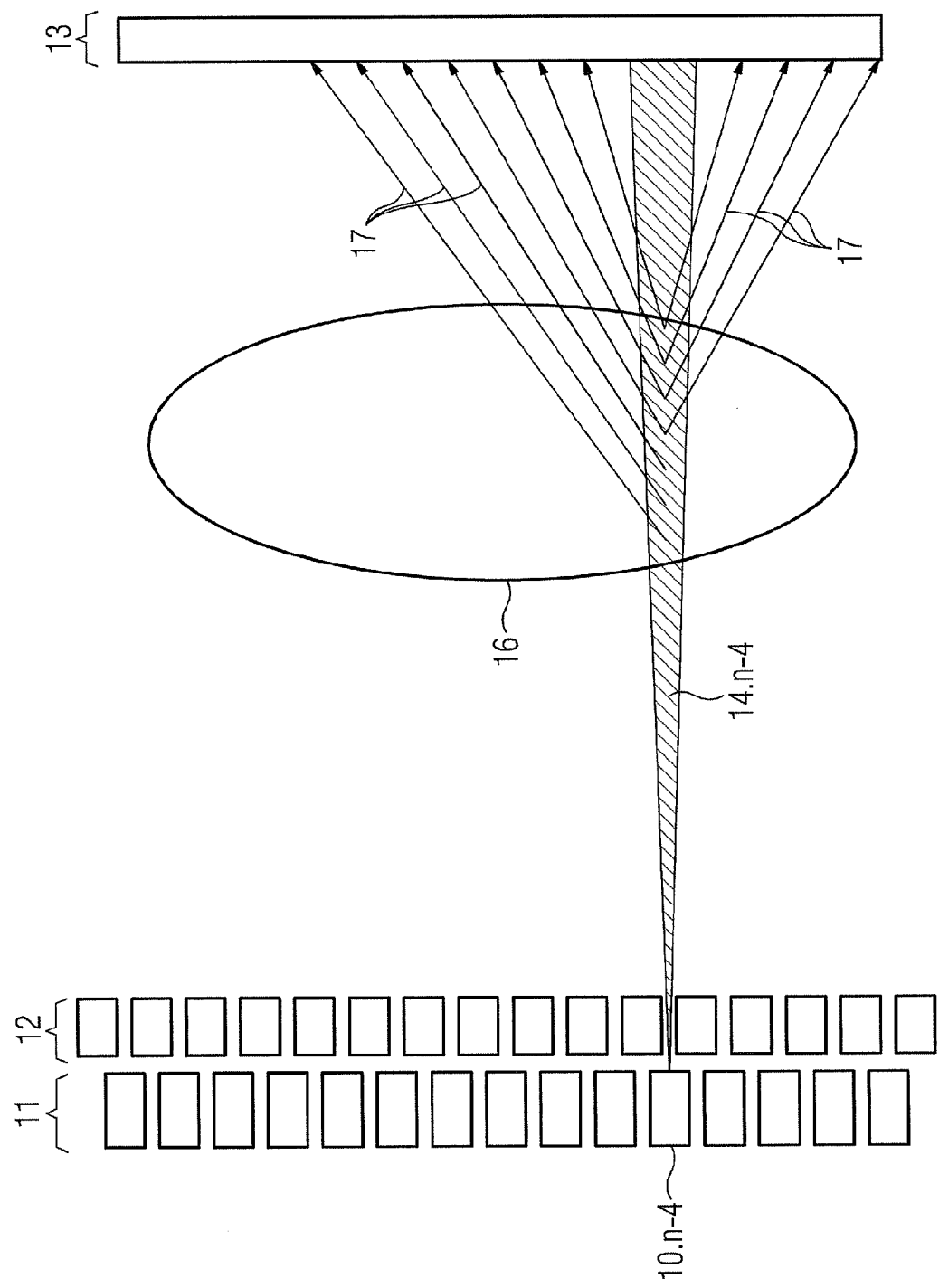

The x-ray emitters are especially activated sequentially in series so that the inventive method can be carried out in accordance with the slot scan method and the area under examination can be recorded in the form of a scan. The sequential activation of the plurality of x-ray emitters of which the x-ray beams are collimated fixed to their respective assigned part areas of the x-ray detector means that the known expensive mechanical movement of collimators known in the prior art for the slot scan method is superfluous, which makes the method faster, simpler and more patient-friendly. The scattered radiation 17 which arises through scattering of x-rays on the object under examination 16 (see FIG. 3) is almost completely avoided since the areas of the x-ray affected by scattered radiation 17 are not being used for imaging at the corresponding time.

As well as a linear array the array can also be formed into a rectangle comprising a plurality of x-ray emitters; other forms are also possible.

The x-ray emitters arranged in the array are especially formed by field emission guns which are embodied to be especially small, light and efficient. The field emission gun features a field emission cathode for generating and emitting electrons in each case. With a field emission cathode electrons are emitted by applying a sufficiently high electrical field. Field emission is achieved for example by a simple diode mode in which a preliminary voltage is applied between anode and cathode. Electrons are emitted by the cathode if the electrical field exceeds the threshold for the emission. A triode construction can also be provided, in which a gate electrode is arranged close to the cathode. Electrons are emitted here by a preliminary voltage being applied between gate and cathode. Subsequently the emitted electrons are accelerated by a high voltage between gate and anode. Field emission cathodes allow a very high, easy-to-control and easily focusable flow of electron beams.

The invention can be briefly summarized as follows: The invention describes a method of recording an x-ray image with an x-ray imaging system with an x-ray source and an x-ray detector, with the x-ray source featuring a plurality of x-ray emitters arranged next to one another, with each x-ray emitter being assigned a part area of the x-ray detector in each case and the x-ray beam generated by the respective x-ray emitter being collimated onto the assigned part area, with a) A first x-ray emitter being activated for emitting a first x-ray beam onto a part area of the x-ray detector assigned to it and image data of the first part area of the x-ray detector being read out.
b) Subsequently a further x-ray emitter for emitting a further x-ray beam onto a further part area of the x-ray detector assigned to it is activated and image data of the further part area of the x-ray detector is read out.
c) Step b) is repeated until such time as image data for all intended part areas, especially all part areas of the x-ray detector, is read out, and
d) The image data of the part areas read out is combined into an x-ray image.

The invention claimed is:

1. A method for recording an x-ray image of an object with an x-ray imaging system having an x-ray source and an x-ray detector, wherein the x-ray source comprises a plurality of x-ray emitters arranged next to each other for emitting x-ray beams, comprising:
   assigning a part area of the x-ray detector to each of the x-ray emitters respectively;
   activating a first x-ray emitter for emitting a first x-ray beam collimated onto a first part area of the x-ray detector assigned to the first x-ray emitter;
   reading out image data of the first part area of the x-ray detector;
   subsequently activating a further x-ray emitter for emitting a further x-ray beam collimated onto a further part area of the x-ray detector assigned to the further x-ray emitter;
   reading out image data of the further part area of the x-ray detector;
   subsequently activating the rest of the x-ray emitters for emitting the rest of the x-ray beams collimated onto part areas of the x-ray detector assigned to the rest of the x-ray emitters respectively until image data for all part areas of the x-ray detector are read out; and
   combining the read out image data for all part areas of the x-ray detector into the x-ray image.

2. The method as claimed in claim 1, wherein each of the x-ray beams is collimated into a slot shape.

3. The method as claimed in claim 1, wherein each of the part areas comprises one to ten pixel lines of the x-ray detector.

4. The method as claimed in claim 1, wherein the all part areas of the x-ray detector together generates an overall surface of the x-ray detector.

5. The method as claimed in claim 1, wherein the x-ray emitters adjacent to each other are activated sequentially in turn.

6. The method as claimed in claim 1, wherein areas of the x-ray detector differing from the emitted part areas are not read out or discarded after reading out.

7. The method as claimed in claim 1, wherein the x-ray emitters are arranged adjacent to each other and assigned to adjacent part areas of the x-ray detector.

8. The method as claimed in claim 1, wherein the x-ray detector is irradiated and read out by a scan.

9. A x-ray imaging system for recording an x-ray image of an object, comprising:
   an x-ray source comprising a plurality of x-ray emitters arranged next to each other for emitting x-ray beams;
   an x-ray detector comprising a plurality of part areas being assigned to the x-ray emitters respectively for reading out image data; and
   a collimator for forming the x-ray beams into slots so that the x-ray beams are collimated onto the part areas of the x-ray detector assigned to the x-ray emitters respectively,
   wherein the x-ray emitters adjacent to each other are configured to be sequentially activated one after another for emitting the x-ray beams collimated onto the part areas of the x-ray detector assigned to the x-ray emitters respectively, and
   wherein the x-ray detector is configured to subsequently read out the image data of the part areas for combining the image data of the part areas into the x-ray image.

10. The x-ray imaging system as claimed in claim 9, wherein the x-ray emitters comprise field emission guns having field emission cathodes.

11. The x-ray imaging system as claimed in claim 10, wherein the field emission cathodes are carbon nanotubes.

12. The x-ray imaging system as claimed in claim 10, wherein the field emission guns are arranged in a linear array.

* * * * *